United States Patent [19]

Takasugi et al.

[11] Patent Number: 5,354,755
[45] Date of Patent: Oct. 11, 1994

[54] 1-ARYL-3-(3,4-DIHYDRO-4-OXO-3-QUINAZOLINYL)UREA FUNGICIDAL AGENTS

[75] Inventors: James J. Takasugi, Horsham, Pa.; Millord V. T. Neypes, Los Banos, Philippines; Lynn S. Evans, Langhorne, Pa.; Clint L. Kohls, Philadelphia, Pa.; Laurie A. Witucki, Stockton, N.J.

[73] Assignee: American Cyanamid Company, Wayne, N.J.

[21] Appl. No.: 35,871

[22] Filed: Apr. 2, 1993

Related U.S. Application Data

[63] Continuation-in-part of Ser. No. 891,528, Jun. 1, 1992, Pat. No. 5,276,038.

[51] Int. Cl.$^5$ .................. A01N 47/36; C07D 239/92
[52] U.S. Cl. ........................ 514/259; 544/287
[58] Field of Search .................. 544/287; 514/259

[56] References Cited

U.S. PATENT DOCUMENTS

| | | | |
|---|---|---|---|
| 3,696,102 | 10/1972 | Cronin | 264/251 |
| 4,521,420 | 6/1985 | Maurer et al. | 514/259 |
| 4,605,657 | 8/1986 | Edwards | 514/259 |
| 5,276,038 | 1/1994 | Takasugi | 514/259 |

FOREIGN PATENT DOCUMENTS

| | | |
|---|---|---|
| 0183458 | 6/1986 | European Pat. Off. . |
| 0360417 | 3/1990 | European Pat. Off. . |

OTHER PUBLICATIONS

Buyuktimkin, Arch. Pharm 318, 496 (1985).
Muruv'eva, Chem Abs 75, 76712 (1971).
Talukdar, Ind J Chem 15B p. 1110 (1977).
Chemical Abstracts, vol. 66, No. 13, (1967) 55462v, p. 5241.
Chemical Abstracts, vol. 89, No. 1 (1978) 6298n, p. 541.
Chemical Abstracts, vol. 108, No. 13 (1988) 112383g. p. 624.
Chemical Abstracts, vol. 68, No. 7 (1968), pp. 2880, 29672k.
Chemical Abstracts, vol. 111, No. 15 (1989) 130542z, p. 419.
A. M. Abbady et al., *Acta Chimica Academiae Scientarm Hungaricae, 91,* pp. 341–349 (1976).
M. F. Abdel–Megeed and A. Teniou, *Revue Roumaine de Chimie, 33,* pp. 981–986 (1988).
Y. A. Ammar et al., *Current Science, 58,* pp. 1231–1234 (1989).
A. P., Bhaduri and N. M. Khanna, *Indian Journal of Chemistry, 4,* pp. 447–449 (1966).
M. T. Bogert and R. A. Gortner, *Journal of the American Chemical Society, 31,* pp. 943–947 (1909).
V. S. Dighe et al., *Current Science, 33,* pp. 78–80 (1984).
T. George et al., *Indian Journal of Chemistry, 9,* pp. 755–758 (1971).
G. Hilgetag and A. Martini (eds.), *Preparative Organic Chemistry,* New York: John Wiley and Sons, 1972, pp. 269 and 472–473.
L. Legrand and L. Lozach, *Bull. Soc. Chim. France,* pp. 1400–1404 (1961).
R. W. Leiby, *Journal of Heterocyclic Chemistry, 21,* pp. 1825–1832 (1984).
R. W. Leiby, *Journal of Organic Chemistry, 50,* pp. 2926–2929 (1985).
R. W. Leiby and N. D. Heindel, *Journal of Organic Chemistry, 42,* pp. 161–162 (1977).
S. Leistner and G. Wagner, *Pharmazie, 35,* pp. 582–584 (1980).
S. R. Nautiyal et al., *Indian Journal of Pharmaceutical Science, 50,* pp. 26–28 (1988).
N. P. Peet et al., *Indian Journal of Chemistry, 14B,* pp. 701–702 (1976).

(List continued on next page.)

*Primary Examiner*—Mark L. Berch
*Attorney, Agent, or Firm*—Michael P. Morris

[57] ABSTRACT

1-Aryl-3-(3,4-dihydro-4-oxo-3-quinazolinyl)urea compounds which are effective for the control or prevention of phytopathogenic fungi are described. A method for the fungicidal use of said compounds and fungicidal compositions containing said compounds is also presented.

16 Claims, No Drawings

OTHER PUBLICATIONS

W. Ried and B. Peters, *Justus Liebigs Ann. Chem.*, 729, pp. 124–138 (1969).

A. Sammour et al., *U.A.R. Journal of Chemistry*, 14, pp. 197–205 (1971).

P. Scheiner et al., *Journal of Heterocyclic Chemistry*, 21, pp. 1817–1824 (1984).

R. Soliman and F. S. G. Soliman, *Synthesis*, 10, pp. 803–804 (1979).

Kumar, *Ind. J. Chem.* 27B, 443 (1988).

Furghaly, *Eur. J. Med. Chem.* 22, 69 (1987).

1-ARYL-3-(3,4-DIHYDRO-4-OXO-3-QUINAZOLINYL)UREA FUNGICIDAL AGENTS

This is a continuation-in-part of copending application serial number 07/891,528 filed on June 1, 1992 now U.S. Pat. No. 5,276,038.

BACKGROUND OF THE INVENTION

Phytopathogenic fungi are the causal agents for many diseases which infect and destroy agronomic crops. Especially devastating are leaf spot type diseases such as banana black sigatoka, sugar beet cercospora leaf spot and peanut leaf spot.

The leaves of the banana plant are subject to attack by a fungus, *Mycosphaerella fijiensis,* causing a disease called banana black sigatoka. Uncontrolled, banana black sigatoka kills the leaves of the banana plant, resulting in small, poor quality fruit. Because banana is a major export for many Latin American countries, the control of banana black sigatoka is critical to those countries' economies.

Currently, only five fungicide classes are used to treat banana black sigatoka. In some areas, the fungus has become resistant to the two most effective of those fungicide classes. The result has been more intensive spraying with the less effective fungicides. Therefore, there is a need for new fungicides with other modes of action for the continued production of banana.

Sugar beet is susceptible to many foliar diseases caused by phytopathogenic fungi. One of the most frequently encountered and most destructive foliar diseases occurring on sugar beet is sugar beet cercospora leaf spot, caused by the fungus, *Cercospora beticola.* Sugar beet cercospora leaf spot is common to sugar beet throughout the world, but is most destructive in regions with wet, warm growing seasons, such as Western and Southern Europe, and the Midwestern United States. During periods of high temperature and wetness, sugar beet cercospora leaf spot spreads rapidly in the field. This disease also kills leaf tissue resulting in reduced sugar beet weight and sugar content.

Peanut leaf spot, caused by fungi of the Mycosphaerella genus, is the most destructive foliar disease of peanut in the southeastern United States. Uncontrolled, peanut leaf spot causes the defoliation of entire fields, resulting in reduced pod size and number. To date, control of peanut leaf spot has been inadequate. Because of the development of resistance to fungicides, and the repeal of approval for other fungicides, ninety-nine percent of peanuts grown in this region are sprayed with a single fungicide. Accordingly, there is ongoing research to create new and more effective fungicides and methods for controlling or preventing such fungal infestations.

Certain quinazolinones have shown useful biological activity (see, e.g., M. T. Bogeft and R. A. Gortner, *J. Amer. Chem. Soc.,* 31, pp. 943–947 (1909); A. P. Bhaduri and N. M. Khanna, *Indian J. Chem,* 4, pages 447–449 (1966); S. Buyuktimkin, *Arch. Pharm.* (Weinheim), 318, pp. 496–501 (1985); K. M. Murav'eva, *Khim.-Farm. Zh.,* 5, pp. 25–27 (1971); P. B. Talukdar, et al, *Indian J. Chem.,* 15B, pp. 1110–1114 (1977); A. Kumar, et al, *Indian J. Chem.,* 27B, pp. 443–447 (1988); and U.S. Pat. No. 3,696,102). None of these documents, however, refers to the use of quinazolinones as fungicides.

EP-A-360417-A published Mar. 28, 1990 relates to derivatives of 4-fluoroanthranilic acid and their use as fungicides. A. M. Farghaly, et al describe the synthesis and antimicrobial evaluation of 2-methyl-3-substituted-4(3H)-quinazolinones in *Eur. J. Med. Chem.,* 22, pp 369–371 (1987). And, Y. A. Ammar, et al describe the antimicrobial activity of 6,8-dichloro-4-(3H)-quinazolinones in *Current Science,* 58, pp. 1231–1234 (1989). However, none of these documents describe the novel compositions and uses provided herein.

It is therefore an object of the present invention to provide 1-aryl-3-(3,4-dihydro-4-oxo-3-quinazolinyl)urea compounds that are highly effective for controlling or preventing phytopathogenic fungal infestations in agronomic crops, both growing and harvested.

It is also an object of the present invention to provide a method for the prevention, control or amelioration of a disease caused by a phytopathogenic fungus by contacting said fungus with a fungicidally effective amount of a 1-aryl-3-(3,4-dihydro-4-oxo-3-quinazolinyl)urea compound.

It is a feature of this invention to provide a method for the prevention, control or amelioration of leaf spot type diseases such as banana black sigatoka, sugar beet cercospora leaf spot and peanut leaf spot.

These and other objects and features of the invention will become more apparent from the detailed description set forth below.

SUMMARY OF THE INVENTION

The present invention describes 1-aryl-3-(3,4-dihydro-4-oxo-3-quinazolinyl)urea compounds which are useful as fungicidal agents.

The 1-aryl-3-(3,4-dihydro-4-oxo-3-quinazolinyl)urea antifungal agents of the present invention have structural formula I:

$$\text{(I)}$$

wherein
X and $X_1$ are each independently hydrogen or fluorine;
Y and $Y_1$ are each independently hydrogen, halogen,
  $C_1$–$C_4$ alkyl optionally substituted with one or more halogen atoms,
  $C_1$–$C_4$ alkoxy optionally substituted with one or more halogen atoms or phenyl,
  nitro,
  cyano,
  hydroxy,
  $C_1$–$C_4$ alkoxycarbonyl,
  $C_1$–$C_4$ alkylcarbonyloxy, or
  phenylcarbonyloxy;
R is hydrogen, $A_2R_3$ or $C_1$–$C_4$ alkyl optionally substituted with one or more halogen atoms;
$R_3$ is hydrogen, $C_1$–$C_4$ alkyl or phenyl optionally substituted with one or more halogen, $C_1$–$C_4$ alkyl or $C_1$–$C_4$ alkoxy groups;
$R_1$ and $R_2$ are each independently hydrogen or $C_1$–$C_4$ alkyl optionally substituted with one or more halogen atoms;
A, $A_1$ and $A_2$ are each independently O or S;

Z, $Z_1$ and $Z_2$ are each independently hydrogen, halogen,
  $C_1$-$C_4$ alkyl optionally substituted with one or more halogen atoms,
  $C_1$-$C_4$ alkoxy optionally substituted with one or more halogen atoms,
  nitro,
  cyano,
  hydroxy,
  $R_4S(O)_n$,
  phenyl,
  phenoxy, or
  $C_1$-$C_4$ alkylcarbonyl; provided that only hydrogen or fluorine can be on positions 2 and 6 of the phenyl ring;
$R_4$ is $C_1$-$C_4$ alkyl optionally substituted with one or more halogen atoms; and
n is an integer of 0, 1 or 2.

The present invention also relates to compositions and methods comprising those compounds for the prevention, control or amelioration of diseases caused by phytopathogenic fungi.

DETAILED DESCRIPTION OF THE INVENTION

Phytopathogenic fungi are the causal agents for many diseases which infect and destroy agronomic crops, both growing and harvested. Especially devastating are leaf spot type diseases such as banana black sigatoka, sugar beet cercospora leaf spot and peanut leaf spot. Accordingly, there is ongoing research to create new and more effective fungicides to prevent or control fungal infestations.

It has now been unexpectedly discovered that certain quinazolinyl urea compounds are highly effective fungicides. The 1-aryl-3-(3,4-dihydro-4-oxo-3-quinazolinyl)urea antifungal agents of the present invention have structural formula I:

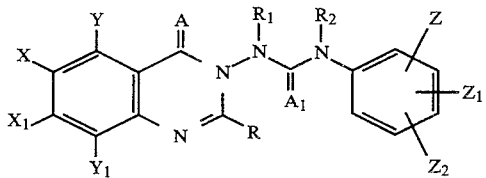

wherein
  X and $X_1$ are each independently hydrogen or fluorine;
  Y and $Y_1$ are each independently hydrogen, halogen,
    $C_1$-$C_4$ alkyl optionally substituted with one or more halogen atoms,
    $C_1$-$C_4$ alkoxy optionally substituted with one or more halogen atoms or phenyl,
    nitro,
    cyano,
    hydroxy,
    $C_1$-$C_4$ alkoxycarbonyl,
    $C_1$-$C_4$ alkylcarbonyloxy, or phenylcarbonyloxy;
  R is hydrogen, $A_2R_3$ or $C_1$-$C_4$ alkyl optionally substituted with one or more halogen atoms;
  $R_3$ is hydrogen, $C_1$-$C_4$ alkyl or phenyl optionally substituted with one or more halogen, $C_1$-$C_4$ alkyl or $C_1$-$C_4$ alkoxy groups;
  $R_1$ and $R_2$ are each independently hydrogen or $C_1$-$C_4$ alkyl optionally substituted with one or more halogen atoms;
  A, $A_1$ and $A_2$ are each independently O or S;
  Z, $Z_1$ and $Z_2$ are each independently hydrogen, halogen,
    $C_1$-$C_4$ alkyl optionally substituted with one or more halogen atoms,
    $C_1$-$C_4$ alkoxy optionally substituted with one or more halogen atoms,
    nitro,
    cyano,
    hydroxy,
    $R_4S(O)_n$,
    phenyl,
    phenoxy, or
    $C_1$-$C_4$ alkylcarbonyl; provided that only hydrogen or fluorine can be on positions 2 and 6 of the phenyl ring;
  $R_4$ is $C_1$-$C_4$ alkyl optionally substituted with one or more halogen atoms; and
  n is an integer of 0, 1 or 2.

Surprisingly, it has been found that the formula I compounds of the present invention are especially useful in the prevention, control or amelioration of leaf spot type diseases such as banana black sigatoka, sugar beet cercospora leaf spot and peanut leaf spot which are caused by the phytopathogenic fungi *Mycosphaerella fijiensis, Cercospora beticola* and *Cercosporidium personatum*, respectively.

Preferred formula I compounds of the present invention which are particularly effective fungicidal agents are those wherein
  X and $X_1$ are hydrogen;
  Y and $Y_1$ are each independently hydrogen or halogen;
  R is hydrogen or $A_2R_3$;
  $R_3$ is $C_1$-$C_4$ alkyl;
  $R_1$ and $R_2$ are hydrogen;
  A is O;
  $A_1$ and $A_2$ are each independently O or S;
  Z is hydrogen; and
  $Z_1$ and $Z_2$ are each independently hydrogen, halogen,
    $C_1$-$C_4$ alkyl substituted with one or more halogen atoms, or
    $C_1$-$C_4$ alkoxy substituted with one or more halogen atoms.

Exemplary of halogen hereinabove are fluorine, chlorine, bromine and iodine.

The present invention also relates to novel 1-aryl-3-(3,4-dihydro-4-oxo-3-quinazolinyl)urea compounds having the following structural formula:

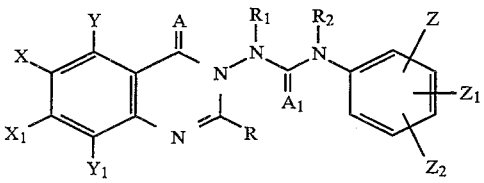

wherein
  X and $X_1$ are each independently hydrogen or fluorine;
  Y and $Y_1$ are each independently hydrogen, halogen,
    $C_1$-$C_4$ alkyl optionally substituted with one or more halogen atoms, $C_1$–$C_4$ alkoxy optionally substituted with one or more halogen atoms or phenyl,
nitro,
cyano,
hydroxy,
$C_1$–$C_4$ alkoxycarbonyl,
$C_1$–$C_4$ alkylcarbonyloxy, or
phenylcarbonyloxy;

R is hydrogen or $A_2R_3$;

$R_3$ is hydrogen, $C_1$–$C_4$ alkyl or phenyl optionally substituted with one or more halogen, $C_1$–$C_4$ alkyl or $C_1$–$C_4$ alkoxy groups;

$R_1$ and $R_2$ are each independently hydrogen or $C_1$–$C_4$ alkyl optionally substituted with one or more halogen atoms;

A, $A_1$ and $A_2$ are each independently O or S;

Z, $Z_1$ and $Z_2$ are each independently hydrogen, halogen,
$C_1$–$C_4$ alkyl optionally substituted with one or more halogen atoms,
$C_1$–$C_4$ alkoxy optionally substituted with one or more halogen atoms,
nitro,
cyano,
hydroxy,
$R_4S(O)_n$,
phenyl,
phenoxy, or
$C_1$–$C_4$ alkylcarbonyl; provided that only hydrogen or fluorine can be on positions 2 and 6 of the phenyl ring;

$R_4$ is $C_1$–$C_4$ alkyl optionally substituted with one or more halogen atoms; and n is an integer of 0, 1 or 2;

provided that when X, $X_1$, Y, $Y_1$, R, $R_1$ and $R_2$ are hydrogen, A is O, and $A_1$ is S, then at least one of Z, $Z_1$ or $Z_2$ is a substituent other than hydrogen.

Certain compounds of formula I may be prepared as shown below in Flow Diagram I.

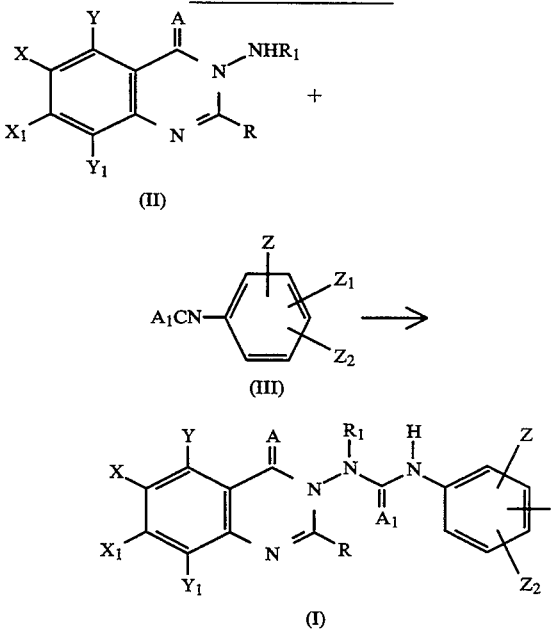

The appropriately substituted formula II compound is reacted with at least one molar equivalent of a formula III substituted cyanate in the presence of an inert organic solvent such as a chlorinated hydrocarbon preferably at a temperature between about 15° and 100° C. to obtain the desired formula I compound.

Other compounds of formula I wherein $R_1$ and $R_2$ are $C_1$–$C_4$ alkyl may be prepared as shown below in flow diagram II.

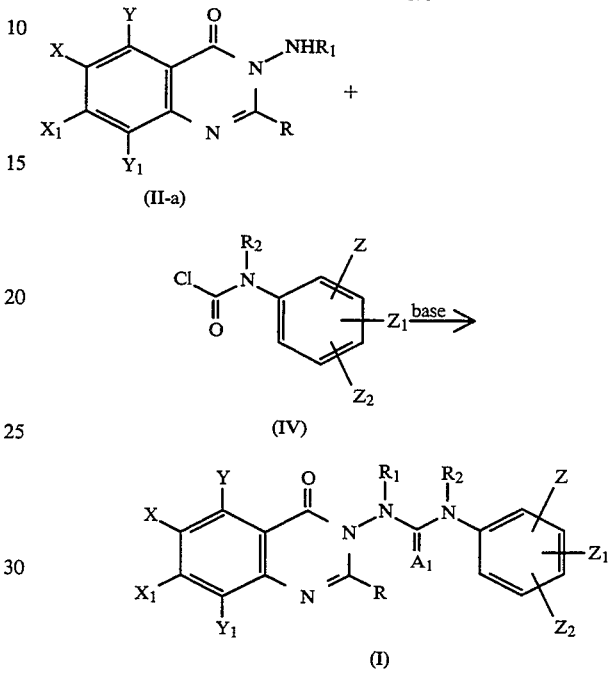

The appropriately substituted formula II-a 3-($C_1$–$C_4$ alkyl)amino-4(3H)quinazolinone is reacted with a formula IV N-($C_1$–$C_4$ alkyl)carbaniloyl chloride in the presence of a base such as pyridine and an inert organic solvent such as a chlorinated hydrocarbon preferably at a temperature between about 15° C. and 100° C. to obtain the desired formula I compound wherein X, $X_1$, Y, $Y_1$, R, Z, $Z_1$ and $Z_2$ are described above for formula I and $R_1$ and $R_2$ are each $C_1$–$C_4$ alkyl (starting formula II compounds are described, e.g., in Journal of Heterocyclic Chemistry, 21, pages 1817–1824 (1984); Journal of Organic Chemistry, 42, pages 161–162 (1977); Journal of Heterocyclic Chemistry, 19, page 117 (1982); and Journal fur praktische Chemie, 31, pages 140–148 (1966). Formula IV and formula III compounds are described in Preparative Organic Chemistry, ed. G. Hilgetag and A. Martini (New York: John Wiley and Sons, 1972), pages 269 and 472–473).

The 1-aryl-3-(3,4-dihydro-4-oxo-3-quinazolinyl)urea compounds of the present invention are effective for preventing, controlling or ameliorating diseases caused by phytopathogenic fungi. The formula I compounds of the invention are especially useful in the prevention, control or amelioration of leaf spot type diseases such as banana black sigatoka, sugar beet cercospora leaf spot and peanut leaf spot.

The 1-aryl-3-(3,4-dihydro-4-oxo-3-quinazolinyl)urea compounds of the present invention are also effective for controlling or preventing the growth of phytopathogenic fungi in the presence of growing or harvested plants when applied to said plants at fungicidally effective rates. The formula I compounds of the invention are especially useful for controlling or preventing the growth of phytopathogenic fungi such as *Mycosphaerella fijiensis*, *Cercospora beticola* and *Cercosporidium personatum* when applied to banana, sugar beet and peanut, respectively.

The present invention also relates to compositions comprising the compounds described above that are useful as fungicides. The amount of compound of the present invention effective as a fungicide will vary somewhat according to the virulence of the target fungus, the environment of the treatment, and the like. Typically, the compositions of the present invention comprise about 1% to 50% by weight, preferably about 10% to 30% by weight, of the formula I compound dispersed in a liquid carrier and when applied to the plant, seed or tuber, or to the soil or water in which they are growing, is effective to protect the plant, seed or tuber from fungal infestation and disease caused thereby.

The formula I compounds are also effective for protecting plants, plant seeds and tubers from fungal infestations and diseases when applied to the plants, plant seeds or tubers in sufficient amount to provide a rate of from about 0.015 kg/ha to about 3.0 kg/ha, preferably from about 0.03 kg/ha to about 2.0 kg/ha, of active ingredient. Obviously, higher rates of application of the formula I compounds may be used to protect plants, plant seeds and tubers from fungal infestations and diseases, for example, for soil applications. Higher rates of application to the plants, plant seeds or tubers, however, are generally unnecessary and wasteful.

The formula I compounds of the invention may be formulated as emulsifiable concentrates, flowable liquid concentrates, or wettable powders which are diluted with water, other suitable polar solvent or oil carrier, generally in situ, and then applied as a dilute spray. Said compounds may also be formulated in dry compacted granules, granular formulations, dusts, dust concentrates, suspension concentrates, microemulsions and the like, all of which lend themselves to seed, tuber, soil, water and/or foliage applications to provide the requisite plant protection. Such formulations include the compounds of the invention admixed with inert, solid or liquid diluents.

For example, wettable powders, dusts and dust concentrate formulations can be prepared by grinding and blending together about 25% to about 85% by weight of formula I compounds and about 75% to about 15% by weight of a solid diluent such as bentonite, diatomaceous earth, kaolin, attapulgite, or the like, about 1% to 5% by weight of a dispersing agent such as sodium lignosulfonate, and about 1% to 5% by weight of a nonionic surfactant, such as octylphenoxy polyethoxy ethanol, nonylphenoxy polyethoxy ethanol, or the like.

A typical flowable liquid concentrate can be prepared by admixing about 40% by weight of the active ingredient with about 2% by weight of a gelling agent such as bentonite, about 3% by weight of a dispersing agent such as sodium lignosulfonate, about 1% by weight of a thickener such as polyethylene glycol, and water.

A typical emulsifiable concentrate can be prepared by dissolving about 5% to 50% by weight of the active ingredient in about 95% to 50% by weight of a solvent such as isophorone, toluene, butyl cellosolve, methyl acetate, propylene glycol monomethyl ether, or the like, and dispersing therein about 1% to 5% by weight of a nonionic surfactant such as an alkylphenoxy polyethoxy alcohol.

The compounds of the invention are prepared for use by adding a predetermined quantity of formulated product, such as described above, to the desired volume of water, other suitable solvent or liquid or solid carrier, alone or in combination with one or more other agronomic chemicals for sequential or simultaneous use. Advantageously, the compounds of the invention may be used effectively in conjunction with, or in combination with, other biological chemicals, including but not limited to, acephate, anilazine, benalaxyl, benomyl, bitertanol, bordeaux mixture, carbendazim, carbofuran, carboxin, capatafol, captan, chlorothalonil, chlorpyrifos, cyproconazole, diazinon, dichloran, diethofencarb, dimethoate, diniconazole, dithianon, dodine, edifenphos, ethoprop, fenamiphos, fenarimol, fenbuconazole, fenfuram, fenpropidin, fenpropimorph, fentin hydroxide, ferbam, flusilazole, flusulfamide, flutriafol, folpet, formothion, fosetyl, fuberidazole, guazatine, hexaconazole, imazalil, iprobenfos, iprodione, malathion, mancozeb, maneb, metalaxyl, methyl parathion, metiram, myclobutanil, nuarimol, ofurace, oxadixyl, oxycarboxin, penconazole, probenazole, prochloraz, propiconazole, pyrazophos, tebuconazole, terbufos, thiabendazole, thiophanate, thiophanate-methyl, triadimefon, triadimenol, triarimol, tricyclazole, tridemorph, triflumizole, triforine, vinclozolin, zineb, and the like.

Where compositions of the invention are to be employed in combination treatments with other pesticidal agents, the composition may be applied as an admixture of the components as described hereinabove or may be applied sequentially.

The present invention provides a method for the prevention, control or amelioration of a disease caused by a phytopathogenic fungus by contacting said fungus with a fungicidally effective amount of a formula I, 1-aryl-3-(3,4-dihydro-4-oxo-3-quinazolinyl)urea compound.

The present invention also provides a method for the protection of a plant, plant seed or tuber from fungal infestation and disease by applying to the plant, plant seed or tuber, or to the soil or water in which they are growing, a fungicidally effective amount of a formula I, 1-aryl-3-(3,4-dihydro-4-oxo-3-quinazolinyl)urea compound.

In order to facilitate a further understanding of the invention, the following examples are presented primarily for the purpose of illustrating more specific details thereof. The examples utilize the above reaction schemes and also provide further means for preparing even more compounds of the present invention which are not specifically described above. The invention is not to be deemed limited thereby except as defined in the claims.

EXAMPLE 1

Preparation of 3-Amino-4(3H)-quinazolinone

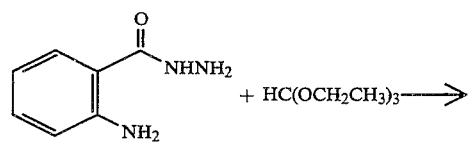

-continued

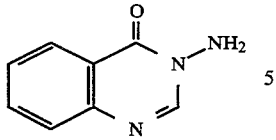

A mixture of 2-aminobenzhydrazide (7.16 g, 47.4 mmol) and triethyl orthoformate (8.3 mL, 49.9 mmol) in ethanol is heated at reflux for 3.5 hours under a nitrogen atmosphere, cooled and filtered to obtain the title product as a white solid, 6.06 g (79%), mp 209°-210.5° C.

Using essentially the same procedure and employing the appropriately substituted 2-aminobenzhydrazide, the following compounds are obtained:

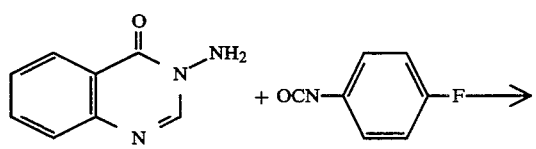

| Y | X | $X_1$ | $Y_1$ | mp °C. |
|---|---|---|---|---|
| H | H | H | $OCH_3$ | 147–149 |
| F | H | H | H | 158–160 |
| H | H | H | Cl | 165–182 |
| H | H | H | $CH_3$ | 174–176 |
| H | H | F | H | 196–200 |
| H | F | H | H | 174.5–176.5 |
| Cl | H | H | H | 169 dec. |

EXAMPLE 2

Preparation of 1-(3,4-Dihydro-4-oxo-3-quinazolinyl)-3-(p-fluorophenyl-)urea

4-Fluorophenyl isocyanate (0.74 mL, 6.51 mmol) is added to a mixture of 3-amino-4(3H)quinazolinone (1.00 g, 6.21 mmol) in 1,2-dichloroethane at reflux. The reaction mixture is heated at reflux for 18 hours, cooled to 0° C. and filtered. The filter cake is washed with ether and dried to give the title product as a white solid, 1.64 g (89%), mp 237°-238° C.

Using essentially the same procedure and employing the appropriately substituted 3-amino-4-(3H)quinazolinone and the appropriate isocyanate, the following compounds are obtained:

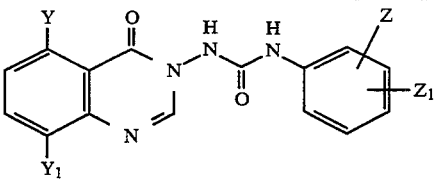

| Y | $Y_1$ | Z | $Z_1$ | mp °C. |
|---|---|---|---|---|
| H | H | 4-Cl | H | |
| H | H | 4-$OCH_3$ | H | 236–237 |
| H | H | 4-$CF_3$ | H | 238–239 |
| H | H | H | H | 219–220 |
| H | H | 3-Cl | 4-Cl | 250.5–251.5 dec. |
| H | H | 4-$CH_3$ | H | 226.5–227.2 |
| H | H | 3-Cl | H | 234.5–236.5 |
| H | H | 2-F | H | 216–217.5 |
| H | H | 4-$NO_2$ | H | 263–280 |
| H | H | 3-Cl | 5-Cl | 257–259 |
| H | H | 4-$OC_6H_5$ | H | 222–228 |
| H | H | 3-$NO_2$ | 4-Cl | 244–245 |
| H | H | 4-Br | H | 225–226 |
| H | H | 3-$OCH_3$ | H | 223–224 |
| H | H | 2-F | 4-F | >250 |
| H | H | 2-F | 6-F | 240–241 |
| H | H | 3-$CH_3$ | H | 219–220 |
| H | H | 3-Br | H | 244–245 |
| H | H | 2-F | 5-F | 231–232 |
| H | H | 4-$OCF_3$ | H | 220–221 |
| H | H | 3-$CF_3$ | H | 246–248 |
| H | H | 3-Cl | 4-$CH_3$ | 262–263 |
| H | H | 3-C(O)$CH_3$ | H | 259–261 |
| H | H | 4-C(O)$CH_3$ | H | 267–269 |
| H | H | 4-I | H | 249–250 |
| H | H | 4-O($CH_2$)$_3CH_3$ | H | 203–204 |
| H | H | 3-$CH_2CH_3$ | H | 224–225 |
| H | H | 3-$CF_3$ | 4-Cl | 239–240 |
| H | H | 3-Cl | 4-F | >260 |
| H | H | 4-$C_6H_5$ | H | 246–248 |
| H | H | 3-CN | H | 248–249 |
| H | H | 4-CN | H | >270 |
| H | H | 4-CH($CH_3$)$_2$ | H | 209–210 |
| H | H | 3-F | H | 204–205 |
| H | H | 4-$SCH_3$ | H | 228–229 |
| H | Cl | 4-Cl | H | 254–256 |
| F | H | 4-Cl | H | |
| F | H | 4-Br | H | 240–243 |
| H | $OCH_3$ | 4-Br | H | 227–229 |
| H | $OCH_3$ | 4-Cl | H | 227–229 |
| H | Cl | 4-Br | H | 268–270 |
| H | $CH_3$ | 4-Br | H | 242–246 dec. |
| H | $CH_3$ | 4-Cl | H | 251–254 |
| H | H | 4-$SCF_3$ | H | 199–201 |

EXAMPLE 3

Preparation of 1-(p-Bromophenyl)-3-(3,4-dihydro-4-oxo-3-quinazolinyl)-2-thiourea

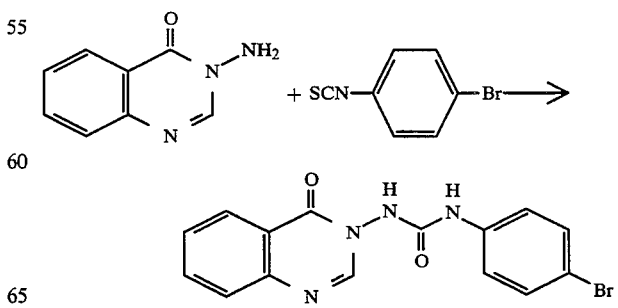

4-Bromophenyl isothiocyanate (2.51 g, 11.72 mmol) is added to a mixture of 3-amino-4(3H)quinazolinone (1.72 g, 10.66 mmol) in 1,2-dichloroethane at reflux under a nitrogen atmosphere. The reaction mixture is heated at reflux for 2 days, cooled, washed with ether and filtered. The filter cake is dried to give the title product as a white solid, 2.44 g, mp 189°–190° C.

Using essentially the same procedure and substituting the appropriate isothiocyanate for 4-bromophenyl isothiocyanate, the following compounds are obtained:

| Z | mp °C. |
|---|---|
| Cl | 172–173.5 |
| NO$_2$ | 180–181 |
| CF$_3$ | 192–194 |
| H | 99–102 |

EXAMPLE 4

Preparation of
3-(p-Chlorophenyl)-1-(3,4-dihydro-4-oxo-3-quinazolinyl)-1-methylurea

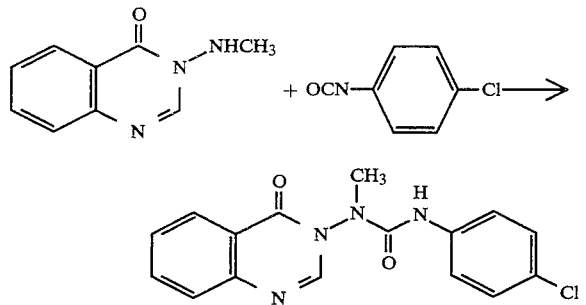

A mixture of 3-methylamino-4(3H)quinazolinone (2.00 g, 11.4 mmol) and 4-chlorophenyl isocyanate 2.01 g, 13.1 mmol) in 1,2-dichloroethane is heated at reflux for 72 hours, concentrated in vacuo and diluted with ether. The organic mixture is heated to reflux and filtered. The filter cake is washed with ether and dried to give the title product as a white solid, 3.61 g (96%), mp 186°–188° C.

EXAMPLE 5

Preparation of 1-(p-Aminophenyl)-3-(3,4-dihydro-4-oxo-3-quinazolinyl)urea

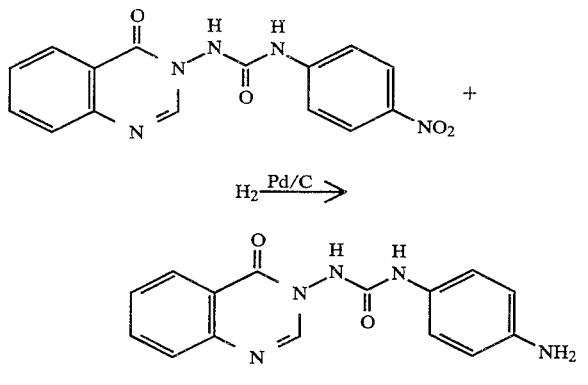

5% Pd/C (0.5 g) is added to a mixture of 1-(3,4-dihydro-4-oxo-3-quinazolinyl)-3-(p-nitrophenyl)urea (1.32 g, 4.06 mmol), ethanol (50 mL) and acetic acid (5 mL). The reaction mixture is placed on a Parr hydrogenator at 50 psi H$_2$ for 3 hours, diluted with acetone and filtered. The filtrate is concentrated in vacuo to obtain a brown oil. The oil is dissolved in methanol, decolorized with activated carbon and concentrated in vacuo to give the title product as a tan solid, 0.9 g, mp>305° C.

EXAMPLE 6

Preparation of
1-(p-Chlorophenyl)-3-(3,4-dihydro-2-ethylthio-4-oxo-3-quinazolinyl)urea

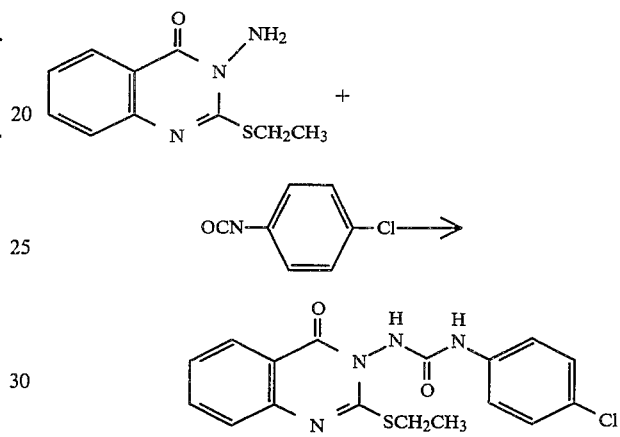

A mixture of 3-amino-2-ethylthio-4-quinazolone (0.60 g, 2.71 mmol) and 4-chlorophenyl isocyanate (0.48 g, 3.13 mmol) in 1,2-dichloroethane is heated at reflux for 63 hours, cooled to 0° C. and filtered. The filter cake is washed with ether and dried to give the title product as a white solid, 0.84 g (83%) mp 234°–235° C.

Using essentially the same procedure, and employing the appropriately substituted 3-amino-4-quinazolone and the appropriately substituted isocyanate, the following compounds are obtained:

| R | Z | mp °C. |
|---|---|---|
| OCH$_2$CH$_3$ | Cl | 210–212 |
| OCH$_2$CH$_3$ | Br | 221–223 |
| SCH$_2$CH$_3$ | Br | 243–244 |
| CH$_3$ | Cl | 228–229.5 |

EXAMPLE 7

Preparation of
1-(p-Chlorophenyl)-3-(3,4-dihydro-4-oxo-3-quinazolinyl)-1,3-dimethylurea

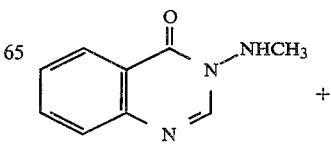

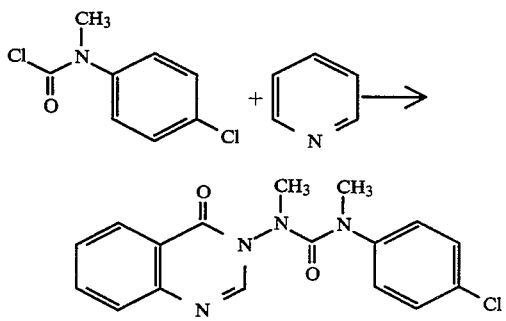

p-Chloro-N-methylcarbaniloyl chloride (1.60 g, 7.84 mmol) is added to a solution of 3-methylamino-4(3H)-quinazolinone (1.36 g, 7.76 mmol) and pyridine (630 μL, 7.79 mmol) in 1,2-dichloroethane. The reaction mixture is heated at reflux for 2 days, concentrated in vacuo, diluted with dichloromethane, washed sequentially with water, 5% hydrochloric acid solution and brine, dried over MgSO₄ and concentrated in vacuo to obtain a tan oil. Chromatography of the oil using silica gel and 20% to 50% ethyl acetate in hexanes solution gives the title product as a white solid, 0.99 g, mp 97°–120° C.

EXAMPLE 8

Preparation of 4-(p-Chlorophenyl)semicarbazide

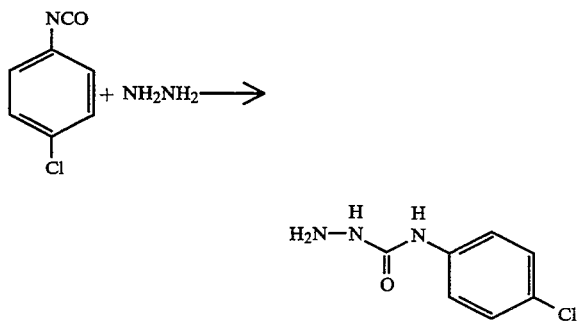

Hydrazine (0.83 mL, 26.4 mmol) is added dropwise to a solution of 4-chlorophenyl isocyanate (3.85 g, 25.1 mmol) in 1,2-dichloroethane. The reaction mixture is stirred overnight at room temperature and filtered. The filter cake is washed with ether and dried to give the title product as a white solid, 4.28 g, which is identified by ¹HNMR spectral analysis.

EXAMPLE 9

Preparation of 2-(Trifluoromethyl)-4H-3,1-benzoxazin-4-one

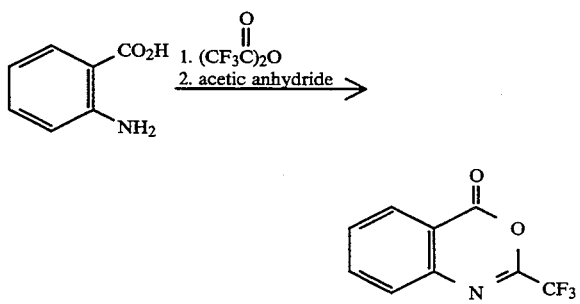

Anthranilic acid (10.07 g, 73.43 mmol) is added portionwise to trifluoroacetic anhydride (31 mL). After the addition is complete, the reaction mixture is concentrated in vacuo to obtain a residue. The residue is diluted with acetic anhydride and the mixture is heated at reflux for 30 minutes, cooled to room temperature and distilled to obtain the title product as a white solid, 13.35 g, which is identified by ¹HNMR spectral analysis.

EXAMPLE 10

Preparation of 1-(p-Chlorophenyl)-3-(3,4-dihydro-4-oxo-2-(trifluoromethyl)-3-quinazolinyl)urea

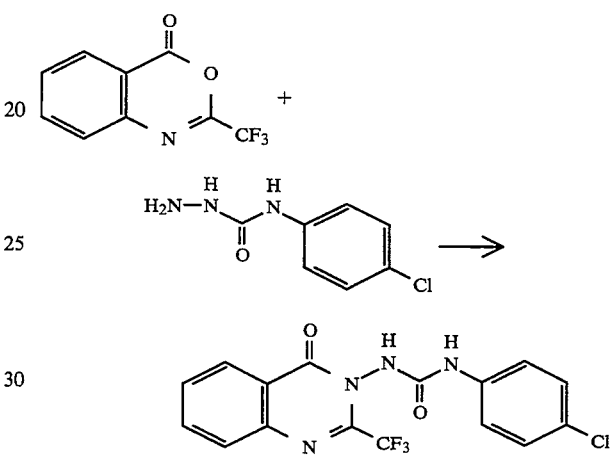

4-(p-Chlorophenyl)semicarbazide (1.49 g, 8.03 mmol) is added to a solution of 2-(trifluoromethyl)-4H-3,1-benzoxazin-4-one (1.72 g, 8.00 mmol) in pyridine (27 mL) at 100° C. The reaction mixture is stirred for 15 hours at 100° C., cooled to room temperature and concentrated in vacuo to obtain a solid. The solid is diluted with dichloromethane and the mixture is washed sequentially with 10% hydrochloric acid and water and concentrated in vacuo to obtain a tan solid. The tan solid is washed with dichloromethane and filtered. The filtrate is concentrated in vacuo to obtain a brown foam. The foam is diluted with ether and the mixture is washed sequentially with 10% hydrochloric acid, water and saturated sodium hydrogen carbonate solution, dried over anhydrous MgSO₄, decolorized with carbon and concentrated in vacuo to obtain a cream colored foam. Flash chromatography of the cream colored foam using silica gel and a 3:1 dichloromethane/hexanes solution gives the title product as a white solid, 0.36 g, which is identified by ¹HNMR spectral analysis.

EXAMPLE 11

Preparation of 1-(p-Bromophenyl)-3-(3,4-dihydro-8-hydroxy-4-oxo-3-quinazolinyl)urea

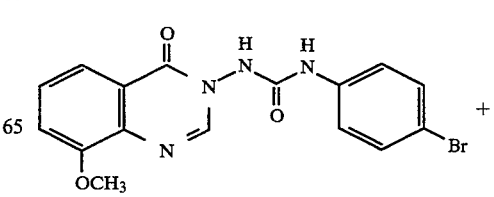

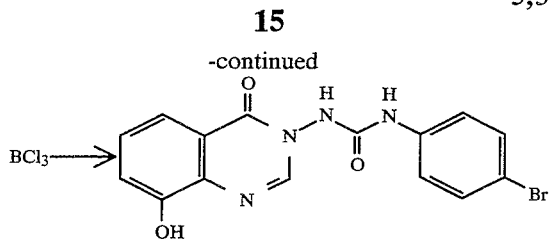

A 1.0 molar solution of boron trichloride in dichloromethane (24 mL, 24.0 mmol BCl₃) is added to a mixture of 1-(p-bromophenyl)-3-(3,4-dihydro-8-methoxy-4-oxo-3-quinazolinyl)urea (3.08 g, 7.91 mmol) in dichloromethane. The reaction mixture is stirred for 20 hours at room temperature, adjusted to about pH 8 with sodium hydrogen carbonate and concentrated in vacuo to obtain a slurry. The slurry is filtered and the filter cake is washed with water and dried to give the title product as a white solid, 2.55 g, mp 276°–278° C., which is identified by ¹HNMR spectral analysis.

Using essentially the same procedure and substituting 1-(p-chlorophenyl)-3-(3,4-dihydro-8-methoxy-4-oxo-3-quinazolinyl)urea for 1-(p-bromophenyl)-3-(3,4-dihydro-8-methoxy-4-oxo-3-quinazolinyl)urea, 1-(p-chlorophenyl)-3-(3,4-dihydro-8-hydroxy-4-oxo-3-quinazolinyl)urea is obtained as a white solid, mp 266°–268° C.

EXAMPLE 12

Preparation of 1-p-Chlorophenyl)-3-(3,4-dihydro-8-hydroxy-4-oxo-3-quinazolinyl)urea acetate (ester)

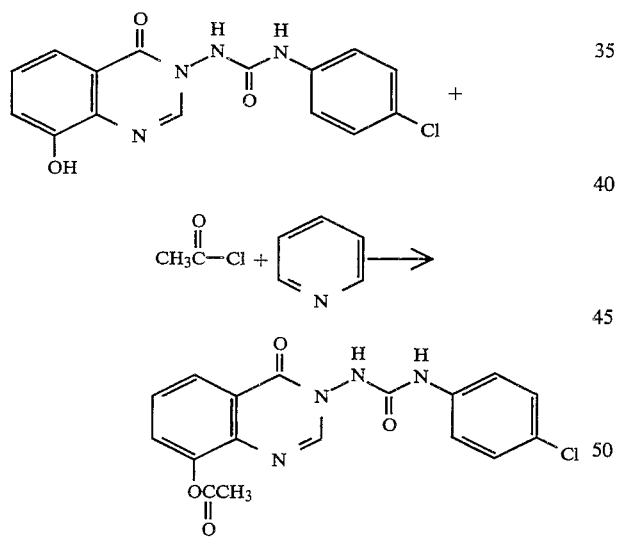

A mixture of 1-(p-chlorophenyl)-3-(3,4-dihydro-8-hydroxy-4-oxo-3-quinazolinyl)urea (0.66 g, 2.00 mmol) in dichloromethane is treated with acetyl chloride (0.155 mL, 2.11 mmol) and pyridine (0.165 mL, 2.04 mmol), stirred overnight, washed sequentially with 5% hydrochloric acid, saturated sodium hydrogen carbonate solution and brine, dried over anhydrous MgSO₄ and concentrated in vacuo to obtain a solid. The solid is washed with dichloromethane and dried to give the title product as a white solid, 0.30 g, mp 216°–218° C., which is identified by ¹HNMR spectral analysis.

Using essentially the same procedure and employing the appropriately substituted 1-(substituted phenyl)-3-(3,4-dihydro-8-hydroxy-4-oxo-3-quinazolinyl)urea and the appropriate acid chloride, the following compounds are obtained:

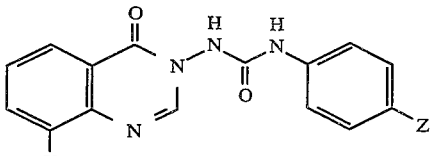

| Y₁ | Z | mp °C. |
|---|---|---|
| —OC(O)CH₃ | Br | 176–178 |
| —OC(O)C₆H₅ | Br | 246–247 |
| —OC(O)C₆H₅ | Cl | 220–221 |

EXAMPLE 13

Preparation of 1-(3,4-Dihydro-4-oxo-3-qinazolinyl)-3-(p-hydroxphenyl)urea

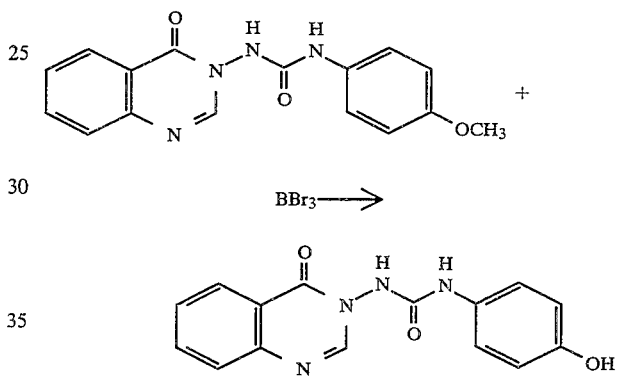

A 1.0 molar solution of boron tribromide (6.45 mL, 6.45 mmol BBr₃) is added dropwise to a mixture of 1-(3,4-dihydro-4-oxo-3-quinazolinyl)-3-(p-methoxyphenyl)urea (1.0 g, 3.22 mmol) in dichloromethane under a nitrogen atmosphere. The reaction mixture is stirred overnight at room temperature, adjusted to about pH 8 with saturated sodium hydrogen carbonate solution, stirred for 2 hours, washed with water and filtered. The filter cake is dried, tri-

EXAMPLE 14

Preparation of 1-(3,4-Dihydro-4-oxo-3-quinazolinyl)-3-{p-[(trifluoromethyl)sulfinyl]phenyl}urea

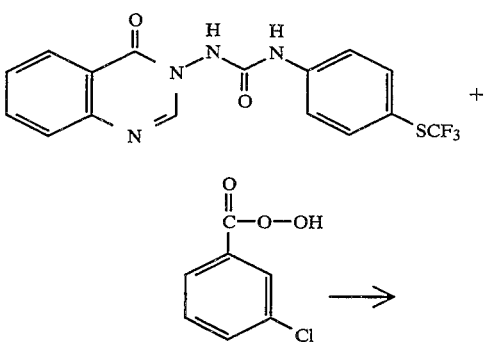

-continued

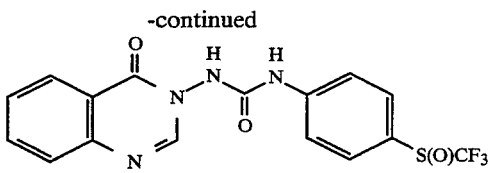

A mixture of 1-(3,4-dihydro-4-oxo-3-quinazolinyl)-3-{p-[(trifluoromethyl)thio]phenyl}urea (1.0 g, 2.63 mmol) in chloroform is cooled with an ice-water bath, treated with a solution of 3-chloroperoxybenzoic acid (0.57 g, 80% real, 2.64 mmol) in chloroform, stirred for 3 hours at 0° C., stirred for 32 hours at room temperature, cooled to 0° C., treated with additional 3-chloroperoxybenzoic acid (0.114 g, 0.53 mmol) in chloroform, stirred for 36 hours at room temperature, diluted with dichloromethane, washed sequentially with saturated sodium sulfite solution, saturated sodium hydrogen carbonate solution and brine, dried over anhydrous MgSO$_4$ and concentrated in vacuo to obtain a yellow solid. Chromatography of the solid using silica gel and a 4:1 ethyl acetate/hexanes solution gives the title product as a white solid, 0.50 g, mp 148°–150° C., which is identified by $^1$HNMR spectral analysis.

Using essentially the same procedure but employing 3.8 equivalents of 3-chloroperoxybenzoic acid, 1-(3,4-dihydro-4-oxo-3-quinazolinyl)-3-{p-[(trifluoromethyl)sulfonyl]phenyl}urea is obtained as a white solid, mp 118°–121° C.

EXAMPLE 15

Evaluation of test compounds against banana black sigatoka caused by *Mycosphaerella fijiensis*

Test compounds are dissolved in acetone and diluted with distilled water containing about 0.05% TWEEN 20 ®, a polyoxyethylene sorbitan monolaurate surfactant manufactured by Atlas Chemical Industries, to give a concentration of 200 ppm.

Banana seedlings at the 6–7 leaf stage are sprayed with test solution on the upper and lower surfaces of the 3 youngest unfurled leaves to the point of run-off, dried and inoculated with a spore suspension of *Mycosphaerella fijiensis*. The inoculated banana seedlings are placed outdoors in a plastic tunnel lined with wet jute sacks. The temperature is maintained between 25° and 32° C. and the relative humidity is maintained between 85% and 100%. After five days, the banana seedlings are transferred to a partially shaded screenhouse, surrounded with wet jute sacks and misted daily. When disease symptom development is optimal, 28 to 40 days post inoculation, the banana seedlings are rated for disease control according to the rating scale shown below. Each test contains inoculated treated plants, inoculated untreated plants and a reference standard.

| Rating Scale | |
|---|---|
| Rating | Range % Control |
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |

-continued

| Rating Scale | |
|---|---|
| Rating | Range % Control |
| 9 | 100 |

When more than one test is run, the data are averaged. The data obtained are shown in Table I.

TABLE I

Evaluation of Test Compounds Against Banana Black Sigatoka

| Compound | Control of Banana Black Sigatoka (200 ppm) |
|---|---|
| 1-(p-Chlorophenyl)-3-(3,4-dihydro-4-oxo-3-quinazolinyl)urea | 8.7 |
| 1-(3,4-Dihydro-4-oxo-3-quinazolinyl)-3-(p-methoxyphenyl)urea | 3.3 |
| 1-(3,4-Dihydro-4-oxo-3-quinazolinyl)-3-(p-fluorophenyl)urea | 7.7 |
| 1-(3,4-Dihydro-4-oxo-3-quinazolinyl)-(α,α,α-trifluoro-p-tolyl)urea | 8.3 |
| 1-(3,4-Dihydro-4-oxo-3-quinazolinyl)-3-phenylurea | 5.0 |
| 1-(3,4-Dichlorophenyl)-3-(3,4-dihydro-4-oxo-3-quinazolinyl)urea | 4.7 |
| 1-(3,4-Dihydro-4-oxo-3-quinazolinyl)-3-(p-tolyl)urea | 6.0 |
| 1-(m-Chlorophenyl)-3-(3,4-dihydro-4-oxo-3-quinazolinyl)urea | 1.7 |
| 1-(3,4-Dihydro-4-oxo-3-quinazolinyl)-3-(o-fluorophenyl)urea | 5.3 |
| 1-(3,5-Dichlorophenyl)-3-(3,4-dihydro-4-oxo-3-quinazolinyl)urea | 0.7 |
| 1-(3,4-Dihydro-4-oxo-3-quinazolinyl)-3-(p-phenoxyphenyl)urea | 0.3 |
| 1-(4-Chloro-3-nitrophenyl)-3-(3,4-dihydro-4-oxo-3-quinazolinyl)urea | 0.0 |
| 3-(p-Chlorophenyl)-1-(3,4-dihydro-4-oxo-3-quinazolinyl)-1-methylurea | 4.0 |
| 1-(p-Aminophenyl)-3-(3,4-dihydro-4-oxo-3-quinazolinyl)urea | 0.3 |
| 1-(p-Bromophenyl)-3-(3,4-dihydro-4-oxo-3-quinazolinyl)urea | 8.7 |
| 1-(3,4-Dihydro-4-oxo-3-quinazolinyl)-3-(m-methoxyphenyl)urea | 0.0 |
| 1-(2,4-Difluorophenyl)-3-(3,4-dihydro-4-oxo-3-quinazolinyl)urea | 4.3 |
| 1-(2,6-Difluorophenyl)-3-(3,4-dihydro-4-oxo-3-quinazolinyl)urea | 5.7 |
| 1-(3,4-Dihydro-4-oxo-3-quinazolinyl)-3-(m-tolyl)urea | 3.0 |
| 1-(m-Bromophenyl)-3-(3,4-dihydro-4-oxo-3-quinazolinyl)urea | 0.0 |
| 1-(2,5-Difluorophenyl)-3-(3,4-dihydro-4-oxo-3-quinazolinyl)urea | 6.0 |
| 1-(p-Chlorophenyl)-3-(3,4-dihydro-4-oxo-3-quinazolinyl)-1,3-dimethylurea | 1.3 |
| 1-(p-Chlorophenyl)-3-(3,4-dihydro-4-oxo-3-quinazolinyl)-2-thiourea | 8.7 |
| 1-(3,4-Dihydro-4-oxo-3-quinazolinyl)-3-[p-(trifluoromethoxy)phenyl]urea | 5.0 |
| 1-(3,4-Dihydro-4-oxo-3-quinazolinyl)-3-(α,α,α-trifluoro-m-tolyl)urea | 0.3 |
| 1-(3-Chloro-p-tolyl)-3-(3,4-dihydro-4-oxo-3-quinazolinyl)urea | 1.7 |
| 1-(m-Acetylphenyl)-3-(3,4-dihydro-4-oxo-3-quinazolinyl)urea | 0.0 |
| 1-(p-Acetylphenyl)-3-(3,4-dihydro-4-oxo-3-quinazolinyl)urea | 5.0 |
| 1-(3,4-Dihydro-4-oxo-3-quinazolinyl)-3-(p-iodophenyl)urea | 8.0 |
| 1-(p-Butoxyphenyl)-3-(3,4-dihydro-4-oxo-3-quinazolinyl)urea | 4.7 |
| 1-(3,4-Dihydro-4-oxo-3-quinazolinyl)-3-(m-ethylphenyl)urea | 1.3 |
| 1-(8-Chloro-3,4-dihydro-4-oxo-3-quinazolinyl)-3-(p-chlorophenyl)urea | 8.7 |
| 1-(p-Chlorophenyl)-3-(5-fluoro-3,4- | 8.0 |

TABLE I-continued

Evaluation of Test Compounds Against Banana Black Sigatoka

| Compound | Control of Banana Black Sigatoka (200 ppm) |
|---|---|
| dihydro-4-oxo-3-quinazolinyl)urea | |
| 1-(3,4-Dihydro-4-oxo-3-quinazolinyl)-3-(3,4-xylyl)urea | 1.3 |
| 1-(4-Chloro-α,α,α-trifluoro-m-tolyl)-3-(3,4-dihydro-4-oxo-3-quinazolinyl)-urea | 0.3 |
| 1-(3-Chloro-4-fluorophenyl)-3-(3,4-dihydro-4-oxo-3-quinazolinyl)urea | 2.0 |
| 1-(4-Biphenyl)-3-(3,4-dihydro-4-oxo-3-quinazolinyl)urea | 1.7 |
| 1-(p-Bromophenyl)-3-(5-fluoro-3,4-dihydro-4-oxo-3-quinazolinyl)urea | 8.0 |
| 1-(p-Bromophenyl)-3-(3,4-dihydro-8-methoxy-4-oxo-3-quinazolinyl)urea | 3.7 |
| 1-(p-Chlorophenyl)-3-(3,4-dihydro-8-methoxy-4-oxo-3-quinazolinyl)urea | 1.0 |
| 1-(m-Cyanophenyl)-3-(3,4-dihydro-4-oxo-3-quinazolinyl)urea | 0.3 |
| 1-(p-Bromophenyl)-3-(8-chloro-3,4-dihydro-4-oxo-3-quinazolinyl)urea | 8.0 |
| 1-(p-Cyanophenyl)-3-(3,4-dihydro-4-oxo-3-quinazolinyl)urea | 4.7 |
| 1-(p-Bromophenyl)-3-(3,4-dihydro-8-methyl-4-oxo-3-quinazolinyl)urea | 4.7 |
| 1-(p-Chlorophenyl)-3-(3,4-dihydro-8-methyl-4-oxo-3-quinazolinyl)urea | 6.7 |
| 1-(3,4-Dihydro-4-oxo-3-quinazolinyl)-3-(m-fluorophenyl)urea | 4.0 |
| 1-(3,4-Dihydro-4-oxo-3-quinazolinyl)-3-(4-fluoro-3-nitrophenyl)urea | 0.3 |
| 1-(p-Chlorophenyl)-3-(3,4-dihydro-2-ethoxy-4-oxo-3-quinazolinyl)urea | 6.3 |
| 1-(p-Bromophenyl)-3-(3,4-dihydro-2-ethoxy-4-oxo-3-quinazolinyl)urea | 4.7 |
| 1-(p-Bromophenyl)-3-(3,4-dihydro-2-ethylthio-4-oxo-3-quinazolinyl)urea | 7.7 |
| 1-(p-Chlorophenyl)-3-(3,4-dihydro-2-ethylthio-4-oxo-3-quinazolinyl)urea | 9.0 |
| 1-(p-Chlorophenyl)-3-(3,4-dihydro-2-methyl-4-oxo-3-quinazolinyl)urea | 5.0 |

EXAMPLE 16

Evaluation of test compounds against sugar beet cercospora leaf spot caused by *Cercospora beticola*

Test compounds are dissolved in acetone and diluted with deionized water containing about 0.05% TWEEN 20 ®, a polyoxyethylene sorbitan monolaurate surfactant manufactured by Atlas Chemical Industries, to give a concentration of 400 ppm.

Two week old beet seedlings are sprayed with test solution to the point of run-off, dried and inoculated with a conidial suspension of *Cercospora beticola*. The inoculated beet seedlings are placed in a moisture chamber. The temperature is maintained between 18° and 22° C. and the relative humidity is maintained at 100%. After five days, the beet seedlings are transferred to a greenhouse and bottom watered daily. When disease symptom development is optimal, 10–14 days post inoculation, the beet seedlings are rated for disease control according to the rating scale shown in Example 15. Each test contains inoculated treated plants, inoculated untreated plants and a reference standard. When more than one test is run, the data are averaged. The data obtained are shown below in Table II.

TABLE II

Evaluation of Test Compounds Against Sugar Beet Cercospora Leaf Spot

| Compound | Control of Sugar Beet Cercospora Leaf Spot (400 ppm) |
|---|---|
| 1-(p-Chlorophenyl)-3-(3,4-dihydro-4-oxo-3-quinazolinyl)urea | 7.3 |
| 1-(3,4-Dihydro-4-oxo-3-quinazolinyl)-3-(p-methoxyphenyl)urea | 4.7 |
| 1-(3,4-Dihydro-4-oxo-3-quinazolinyl)-3-(p-fluorophenyl)urea | 6.7 |
| 1-(3,4-Dihydro-4-oxo-3-quinazolinyl)-(α,α,α-trifluoro-p-tolyl)-urea | 7.3 |
| 1-(3,4-Dihydro-4-oxo-3-quinazolinyl)-3-phenylurea | 6.0 |
| 1-(3,4-Dichlorophenyl)-3-(3,4-dihydro-4-oxo-3-quinazolinyl)urea | 4.3 |
| 1-(3,4-Dihydro-4-oxo-3-quinazolinyl)-3-(p-tolyl)urea | 7.3 |
| 1-(m-Chlorophenyl)-3-(3,4-dihydro-4-oxo-3-quinazolinyl)urea | 5.3 |
| 1-(3,4-Dihydro-4-oxo-3-quinazolinyl)-3-(o-fluorophenyl)urea | 6.7 |
| 1-(3,4-Dihydro-4-oxo-3-quinazolinyl)-3-(p-nitrophenyl)urea | 4.7 |
| 1-(3,5-Dichlorophenyl)-3-(3,4-dihydro-4-oxo-3-quinazolinyl)urea | 2.3 |
| 1-(3,4-Dihydro-4-oxo-3-quinazolinyl)-3-(p-phenoxyphenyl)urea | 5.7 |
| 1-(4-Chloro-3-nitrophenyl)-3-(3,4-dihydro-4-oxo-3-quinazolinyl)urea | 2.0 |
| 3-(p-Chlorophenyl)-1-(3,4-dihydro-4-oxo-3-quinazolinyl)-1-methylurea | 0.3 |
| 1-(p-Aminophenyl)-3-(3,4-dihydro-4-oxo-3-quinazolinyl)urea | 3.3 |
| 1-(p-Bromophenyl)-3-(3,4-dihydro-4-oxo-3-quinazolinyl)urea | 7.7 |
| 1-(3,4-Dihydro-4-oxo-3-quinazolinyl)-3-(m-methoxyphenyl)urea | 2.3 |
| 1-(2,4-Difluorophenyl)-3-(3,4-dihydro-4-oxo-3-quinazolinyl)urea | 3.3 |
| 1-(2,6-Difluorophenyl)-3-(3,4-dihydro-4-oxo-3-quinazolinyl)urea | 6.0 |
| 1-(3,4-Dihydro-4-oxo-3-quinazolinyl)-3-(m-tolyl)urea | 2.3 |
| 1-(m-Bromophenyl)-3-(3,4-dihydro-4-oxo-3-quinazolinyl)urea | 2.7 |
| 1-(2,5-Difluorophenyl)-3-(3,4-dihydro-4-oxo-3-quinazolinyl)urea | 7.0 |
| 1-(p-Chlorophenyl)-3-(3,4-dihydro-4-oxo-3-quinazolinyl)-1,3-dimethylurea | 5.3 |
| 1-(p-Chlorophenyl)-3-(3,4-dihydro-4-oxo-3-quinazolinyl)-2-thiourea | 6.7 |
| 1-(3,4-Dihydro-4-oxo-3-quinazolinyl)-3-[p-(trifluoromethoxy)phenyl]urea | 1.3 |
| 1-(3,4-Dihydro-4-oxo-3-quinazolinyl)-3-(α,α,α-trifluoro-m-tolyl)urea | 3.3 |
| 1-(3-Chloro-p-tolyl)-3-(3,4-dihydro-4-oxo-3-quinazolinyl)urea | 0.0 |
| 1-(m-Acetylphenyl)-3-(3,4-dihydro-4-oxo-3-quinazolinyl)urea | 1.6 |
| 1-(p-Acetylphenyl)-3-(3,4-dihydro-4-oxo-3-quinazolinyl)urea | 0.6 |
| 1-(3,4-Dihydro-4-oxo-3-quinazolinyl)-3-(p-iodophenyl)urea | 0.6 |
| 1-(p-Butoxyphenyl)-3-(3,4-dihydro-4-oxo-3-quinazolinyl)urea | 0.0 |
| 1-(3,4-Dihydro-4-oxo-3-quinazolinyl)-3-(m-ethylphenyl)urea | 0.0 |
| 1-(8-Chloro-3,4-dihydro-4-oxo-3-quinazolinyl)-3-(p-chlorophenyl)urea | 2.0 |
| 1-(p-Chlorophenyl)-3-(5-fluoro-3,4-dihydro-4-oxo-3-quinazolinyl)urea | 7.7 |
| 1-(4-Chloro-α,α,α-trifluoro-m-tolyl)-3-(3,4-dihydro-4-oxo-3-quinazolinyl)urea | 1.0 |
| 1-(3-Chloro-4-fluorophenyl)-3-(3,4-dihydro-4-oxo-3-quinazolinyl)urea | 1.0 |

TABLE II-continued

Evaluation of Test Compounds Against
Sugar Beet Cercospora Leaf Spot

| Compound | Control of Sugar Beet Cercospora Leaf Spot (400 ppm) |
|---|---|
| 1-(4-Biphenyl)-3-(3,4-dihydro-4-oxo-3-quinazolinyl)urea | 0.0 |
| 1-(p-Bromophenyl)-3-(5-fluoro-3,4-dihydro-4-oxo-3-quinazolinyl)urea | 8.6 |
| 1-(p-Bromophenyl)-3-(3,4-dihydro-8-methoxy-4-oxo-3-quinazolinyl)urea | 0.0 |
| 1-(p-Chlorophenyl)-3-(3,4-dihydro-8-methoxy-4-oxo-3-quinazolinyl)urea | 0.0 |
| 1-(m-Cyanophenyl)-3-(3,4-dihydro-4-oxo-3-quinazolinyl)urea | 0.7 |
| 1-(p-Bromophenyl)-3-(8-chloro-3,4-dihydro-4-oxo-3-quinazolinyl)urea | 4.0 |
| 1-(p-Cyanophenyl)-3-(3,4-dihydro-4-oxo-3-quinazolinyl)urea | 4.7 |
| 1-(p-Bromophenyl)-3-(3,4-dihydro-8-methyl-4-oxo-3-quinazolinyl)urea | 1.0 |
| 1-(p-Chlorophenyl)-3-(3,4-dihydro-8-methyl-4-oxo-3-quinazolinyl)urea | 6.0 |
| 1-(3,4-Dihydro-4-oxo-3-quinazolinyl)-3-(p-isopropylphenyl)urea | 2.7 |
| 1-(3,4-Dihydro-4-oxo-3-quinazolinyl)-3-(m-fluorophenyl)urea | 5.0 |
| 1-(3,4-Dihydro-4-oxo-3-quinazolinyl)-3-(3,4-xylyl)urea | 1.0 |
| 1-(3,4-Dihydro-4-oxo-3-quinazolinyl)-3-(4-fluoro-3-nitrophenyl)urea | 3.3 |
| 1-(p-Bromophenyl)-3-(6-fluoro-3,4-dihydro-4-oxo-3-quinazolinyl)urea | 5.0 |
| 1-(p-Bromophenyl)-3-(7-fluoro-3,4-dihydro-4-oxo-3-quinazolinyl)urea | 0.0 |
| 1-(p-Chlorophenyl)-3-(7-fluoro-3,4-dihydro-4-oxo-3-quinazolinyl)urea | 1.3 |
| 1-(p-Chlorophenyl)-3-(3,4-dihydro-2-ethoxy-4-oxo-3-quinazolinyl)urea | 1.0 |
| 1-(p-Bromophenyl)-3-(3,4-dihydro-2-ethoxy-4-oxo-3-quinazolinyl)urea | 0.7 |
| 1-(p-Bromophenyl)-3-(3,4-dihydro-2-ethylthio-4-oxo-3-quinazolinyl)urea | 0.0 |
| 1-(p-Chlorophenyl)-3-(3,4-dihydro-2-ethylthio-4-oxo-3-quinazolinyl)urea | 0.7 |
| 1-(p-Chlorophenyl)-3-(3,4-dihydro-2-methyl-4-oxo-3-quinazolinyl)urea | 7.3 |

EXAMPLE 17

Evaluation of test compounds against peanut late leaf spot caused by *Cercosporidium personatum*

Test compounds are formulated in an acetone/Triton X-155 ® (an octylphenoxy polyethoxy-ethanol dispersant manufactured by Rohm and Haas Co.) aqueous solution (5%/0.1% v/v), to give concentrations of 200 and 100 ppm.

Peanut plants are sprayed with test solution, dried and inoculated with conidia of *Cercosporidium personatum*. When disease symptom development is optimal the peanut plants are rated for disease control according to the equation:

$$\% \text{ control} = \frac{\text{number of lesions on check plants} - \text{number of lesions on treated plants}}{\text{number of lesions on check plants}} \times 100$$

Each test contains inoculated treated plants, inoculated untreated plants and a reference standard. When more than one test is run, the data are averaged. The data obtained are shown below in Table III.

TABLE III

Evaluation of Test Compounds Against
Peanut Late Leaf Spot

| Compound | Rate (ppm) | % Control of Peanut Late Leaf Spot |
|---|---|---|
| 1-(p-Chlorophenyl)-3-(3,4-dihydro-4-oxo-3-quinazolinyl)urea | 200 | 100 |
| | 100 | 99 |
| 1-(p-Chlorophenyl)-3-(3,4-dihydro-4-oxo-3-quinazolinyl)-2-thiourea | 200 | 100 |
| | 100 | 100 |
| 1-(3,4-Dihydro-4-oxo-3-quinazolinyl)-3-(p-fluorophenyl)urea | 200 | 95 |
| | 100 | 86 |
| 1-(p-Chlorophenyl)-3-(5-fluoro-3,4-dihydro-4-oxo-3-quinazolinyl)urea | 200 | 79 |
| | 100 | 85 |
| 1-(3,4-Dihydro-4-oxo-3-quinazolinyl)-3-(p-fluorophenyl)-2-thiourea | 200 | 81 |
| | 100 | 90 |
| 1-(3,4-Dihydro-4-oxo-3-quinazolinyl)-3-(α,α,α-trifluoro-p-tolyl)urea | 200 | 98 |
| | 100 | 93 |
| 1-(p-Bromophenyl)-3-(3,4-dihydro-4-oxo-3-quinazolinyl)urea | 200 | 100 |
| | 100 | 93 |
| 1-(8-Chloro-3,4-dihydro-4-oxo-3-quinazolinyl)-3-(p-chlorophenyl)urea | 200 | 96 |
| | 100 | 89 |
| 1-(p-Bromophenyl)-3-(5-fluoro-3,4-dihydro-4-oxo-3-quinazolinyl)urea | 200 | 94 |
| | 100 | 81 |
| 1-(p-Bromophenyl)-3-(3,4-dihydro-4-oxo-3-quinazolinyl)-2-thiourea | 200 | 99 |
| | 100 | 90 |

EXAMPLE 18

Soil systemic evaluation of test compounds against sugar beet cercospora leaf spot caused by *Cercospora beticola*

Test solutions are prepared by dissolving test compounds in acetone and diluting with deionized water containing about 0.05% TWEEN 20 ® a polyoxyethylene sorbitan monolaurate surfactant manufactured by Atlas Chemical Industries.

Test solution is applied to the soil surface of pots containing five week old beet seedlings in sufficient quantity to provide the equivalent of about 2.5 to 10.0 kilograms per hectare of test compound per pot. After three days, the beet seedlings are inoculated with a conidial suspension of *Cercospora beticola*. The inoculated beet seedlings are placed in a moisture chamber for five days, transferred to a greenhouse and bottom watered daily. When disease symptom development is optimal, 10-14 days post inoculation, the beet seedlings are rated for disease control according to the rating scale shown in Example 15. Each test contains inoculated treated plants, inoculated untreated plants and a reference standard. When more than one test is run, the data are averaged. The data obtained are shown below in Table IV.

TABLE IV

Soil Systemic Evaluation of Test Compounds
Against Sugar Beet Cercospora Leaf Spot

| Compound | Rate (kg/ha) | Control of Sugar Beet Cercospora Leaf Spot |
|---|---|---|
| 1-(p-Chlorophenyl)-3-(3,4-dihydro-4-oxo-3-quinazolinyl)urea | 10.0 | 8.7 |
| | 5.0 | 8.0 |
| | 2.5 | 9.0 |
| 1-(p-Chlorophenyl)-3- | 10.0 | 5.7 |

TABLE IV-continued

Soil Systemic Evaluation of Test Compounds Against Sugar Beet Cercospora Leaf Spot

| Compound | Rate (kg/ha) | Control of Sugar Beet Cercospora Leaf Spot |
| --- | --- | --- |
| (3,4-dihydro-4-oxo-3-quinazolinyl)-2-thiourea | 5.0 | 7.3 |
| 1-(p-Chlorophenyl)-3-(5-fluoro-3,4-dihydro-4-oxo-3-quinazolinyl)-urea | 10.0 5.0 | 7.0 4.7 |
| 1-(3,4-Dihydro-4-oxo-3-quinazolinyl)-3-(α,α,α-trifluoro-p-tolyl)urea | 10.0 5.0 | 5.0 6.0 |
| 1-(p-Bromophenyl)-3-(3,4-dihydro-4-oxo-3-quinazolinyl)urea | 10.0 5.0 | 5.3 6.3 |
| 1-(8-Chloro-3,4-dihydro-4-oxo-3-quinazolinyl)-3-(p-chlorophenyl)urea | 10.0 5.0 | 2.3 2.0 |

What is claimed is:

1. A compound having the structure wherein

X and $X_1$ are each independently hydrogen or fluorine;

Y and $Y_1$ are each independently hydrogen, halogen, $C_1$-$C_4$ alkyl optionally substituted with one or more halogen atoms,
$C_1$-$C_4$ alkoxy optionally substituted with one or more halogen atoms or phenyl,
nitro,
cyano,
hydroxy,
$C_1$-$C_4$ alkoxycarbonyl,
$C_1$-$C_4$ alkylcarbonyloxy, or phenylcarbonyloxy;

R is $A_2R_3$;

$R_3$ is hydrogen, $C_1$-$C_4$ alkyl or phenyl optionally substituted with one or more halogen, $C_1$-$C_4$ alkyl or $C_1$-$C_4$ alkoxy groups;

$R_1$ and $R_2$ are each independently hydrogen or $C_1$-$C_4$ alkyl optionally substituted with one or more halogen atoms;

A, $A_1$ and $A_2$ are each independently O or S;

Z, $Z_1$ and $Z_2$ are each independently hydrogen, halogen,
$C_1$-$C_4$ alkyl optionally substituted with one or more halogen atoms,
$C_1$-$C_4$ alkoxy optionally substituted with one or more halogen atoms,
nitro,
cyano,
hydroxy,
$R_4S(O)_n$,
phenyl,
phenoxy, or
$C_1$-$C_4$ alkylcarbonyl; provided that only hydrogen or fluorine can be on positions 2 and 6 of the phenyl ring;

$R_4$ is $C_1$-$C_4$ alkyl optionally substituted with one or more halogen atoms; and n is an integer of 0, 1 or 2.

2. The compound according to claim 1 wherein
X and $X_1$ are hydrogen;
Y and $Y_1$ are each independently hydrogen or halogen;
R is $A_2R_3$;
$R_3$ is $C_1$-$C_4$ alkyl;
$R_1$ and $R_2$ are hydrogen;
A is O;
$A_1$ and $A_2$ are each independently O or S;
Z is hydrogen; and
$Z_1$ and $Z_2$ are each independently hydrogen, halogen,
$C_1$-$C_4$ alkyl substituted with one or more halogen atoms, or
$C_1$-$C_4$ alkoxy substituted with one or more halogen atoms.

3. The compound according to claim 2 which is 1-(p-chlorophenyl)-3-(3,4-dihydro-2-ethylthio-4-oxo-3-quinazolinyl)urea.

4. A method for the prevention, control or amelioration of a disease caused by a phytopathogenic fungus which comprises contacting said fungus with a fungicidally effective amount of a compound have the structure wherein X and $X_1$ are each independently hydrogen or fluorine;

Y and $Y_1$ are each independently hydrogen, halogen,
$C_1$-$C_4$ alkyl optionally substituted with one or more halogen atoms,
$C_1$-$C_4$ alkoxy optionally substituted with one or more halogen atoms or phenyl,
nitro,
cyano,
hydroxy,
$C_1$-$C_4$ alkoxycarbonyl,
$C_1$-$C_4$ alkylcarbonyloxy, or
phenylcarbonyloxy;

R is $A_2R_3$;

$R_3$ is hydrogen, $C_1$-$C_4$ alkyl or phenyl optionally substituted with one or more halogen, $C_1$-$C_4$ alkyl or $C_1$-$C_4$ alkoxy groups;

$R_1$ and $R_2$ are each independently hydrogen or $C_1$-$C_4$ alkyl optionally substituted with one or more halogen atoms;

A, $A_1$ and $A_2$ are each independently O or S;

Z, $Z_1$ and $Z_2$ are each independently hydrogen, halogen,
$C_1$-$C_4$ alkyl optionally substituted with one or more halogen atoms,
$C_1$-$C_4$ alkoxy optionally substituted with one or more halogen atoms,
nitro,
cyano,
hydroxy,
$R_4S(O)_n$, phenyl,
phenoxy, or
$C_1$-$C_4$ alkylcarbonyl; provided that only hydrogen or fluorine can be on positions 2 and 6 of the phenyl ring;

$R_4$ is $C_1$-$C_4$ alkyl optionally substituted with one or more halogen atoms; and n is an integer of 0, 1 or 2.

5. The method according to claim 4 wherein the disease is selected from the group consisting of banana black sigatoka, sugar beet cercospora leaf spot and peanut leaf spot.

6. The method according to claim 4 wherein the phytopathogenic fungus is selected from the group consisting of *Mycosphaerella fijiensis, Cercospora beticola* and *Cercosporidium personatum.*

7. The method according to claim 4 wherein

X and $X_1$ are hydrogen;

Y and $Y_1$ are each independently hydrogen or halogen;

R is $A_2R_3$;

$R_3$ is $C_1$-$C_4$ alkyl;

$R_1$ and $R_2$ are hydrogen;

A is O;

$A_1$ and $A_2$ are each independently O or S;

Z is hydrogen; and $Z_1$ and $Z_2$ are each independently hydrogen, halogen,
$C_1$-$C_4$ alkyl substituted with one or more halogen atoms, or
$C_1$-$C_4$ alkoxy substituted with one or more halogen atoms.

8. The method according to claim 7 wherein the compound is
1-(p-chlorophenyl)-3-(3,4-dihydro-2-ethylthio-4-oxo-3-quinazolinyl)urea.

9. A method for the protection of a plant, plant seed or tuber from fungal infestation and disease which comprises applying to the plant, plant seed or tuber, or to the soil or water in which they are growing, a fungicidally effective amount of a compound having the structure

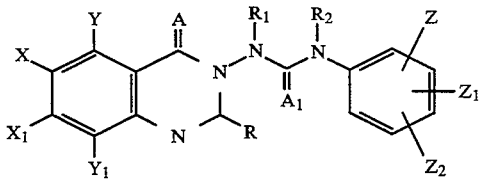

wherein

X and $X_1$ are each independently hydrogen or fluorine;

Y and $Y_1$ are each independently hydrogen, halogen,
$C_1$-$C_4$ alkyl optionally substituted with one or more halogen atoms,
$C_1$-$C_4$ alkoxy optionally substituted with one or more halogen atoms or phenyl,
nitro,
cyano,
hydroxy,
$C_1$-$C_4$ alkoxycarbonyl,
$C_1$-$C_4$ alkylcarbonyloxy, or
phenylcarbonyloxy;

R is $A_2R_3$;

$R_3$ is hydrogen, $C_1$-$C_4$ alkyl or phenyl optionally substituted with one or more halogen, $C_1$-$C_4$ alkyl or $C_1$-$C_4$ alkoxy groups;

$R_1$ and $R_2$ are each independently hydrogen or $C_1$-$C_4$ alkyl optionally substituted with one or more halogen atoms;

A, $A_1$ and $A_2$ are each independently O or S;

Z, $Z_1$ and $Z_2$ are each independently hydrogen, halogen,
$C_1$-$C_4$ alkyl optionally substituted with one or more halogen atoms,
$C_1$-$C_4$ alkoxy optionally substituted with one or more halogen atoms,
nitro,
cyano,
hydroxy,
$R_4S(O)_n$,
phenyl,
phenoxy, or
$C_1$-$C_4$ alkylcarbonyl; provided that only hydrogen or fluorine can be on positions 2 and 6 of the phenyl ring;

$R_4$ is $C_1$-$C_4$ alkyl optionally substituted with one or more halogen atoms; and n is an integer of 0, 1 or 2.

10. The method according to claim 9 wherein the plant is selected from the group consisting of banana, sugar beet and peanut.

11. The method according to claim 9 wherein the fungal disease is selected from the group consisting of banana black sigatoka, sugar beet cercospora leaf spot and peanut leaf spot.

12. The method according to claim 9 wherein

X and $X_1$ are hydrogen;

Y and $Y_1$ are each independently hydrogen or halogen;

R is $A_2R_3$;

$R_3$ is $C_1$-$C_4$ alkyl;

$R_1$ and $R_2$ are hydrogen;

A is O;

$A_1$ and $A_2$ are each independently O or S;

Z is hydrogen; and $Z_1$ and $Z_2$ are each independently hydrogen, halogen,
$C_1$-$C_4$ alkyl substituted with one or more halogen atoms, or
$C_1$-$C_4$ alkoxy substituted with one or more halogen atoms.

13. The method according to claim 12 wherein the compound is
1-(p-chlorophenyl)-3-(3,4-dihydro-2-ethylthio-4-oxo-3-quinazolinyl)urea.

14. The method according to claim 9 wherein the compound is applied to the plant at a rate of about 0.015 kg/ha to about 3.0 kg/ha.

15. A composition for controlling phytopathogenic fungi which comprises an inert liquid or solid diluent and a fungicidally effective amount of a compound having the structure

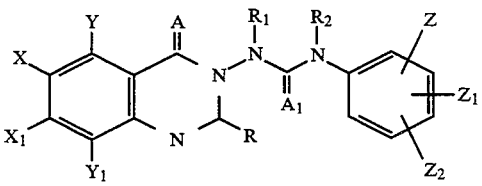

wherein
- X and $X_1$ are each independently hydrogen or fluorine;
- Y and $Y_1$ are each independently hydrogen, halogen,
    - $C_1$–$C_4$ alkyl optionally substituted with one or more halogen atoms,
    - $C_1$–$C_4$ alkoxy optionally substituted with one or more halogen atoms or phenyl,
    - nitro,
    - cyano,
    - hydroxy,
    - $C_1$–$C_4$ alkoxycarbonyl,
    - $C_1$–$C_4$ alkylcarbonyloxy, or
    - phenylcarbonyloxy;
- R is $A_2R_3$;
- $R_3$ is hydrogen, $C_1$–$C_4$ alkyl or phenyl optionally substituted with one or more halogen, $C_1$–$C_4$ alkyl or $C_1$–$C_4$ alkoxy groups;
- $R_1$ and $R_2$ are each independently hydrogen or $C_1$–$C_4$ alkyl optionally substituted with one or more halogen atoms;
- A, $A_1$ and $A_2$ are each independently O or S;
- Z, $Z_1$ and $Z_2$ are each independently hydrogen, halogen,
    - $C_1$–$C_4$ alkyl optionally substituted with one or more halogen atoms,
    - $C_1$–$C_4$ alkoxy optionally substituted with one or more halogen atoms,
    - nitro,
    - cyano,
    - hydroxy,
    - $R_4S(O)_n$,
    - phenyl,
    - phenoxy, or
    - $C_1$–$C_4$ alkylcarbonyl; provided that only hydrogen or fluorine can be on positions 2 and 6 of the phenyl ring;
- $R_4$ is $C_1$–$C_4$ alkyl optionally substituted with one or more halogen atoms; and
- n is an integer of 0, 1 or 2.

16. The composition according to claim 15 wherein
- X and $X_1$ are hydrogen;
- Y and $Y_1$ are each independently hydrogen or halogen;
- R is $A_2R_3$;
- $R_3$ is $C_1$–$C_4$ alkyl;
- $R_1$ and $R_2$ are hydrogen;
- A is O;
- $A_1$ and $A_2$ are each independently O or S;
- Z is hydrogen; and
- $Z_1$ and $Z_2$ are each independently hydrogen, halogen,
    - $C_1$–$C_4$ alkyl substituted with one or more halogen atoms, or
    - $C_1$–$C_4$ alkoxy substituted with one or more halogen atoms.

* * * * *